United States Patent
Qian et al.

(10) Patent No.: US 8,940,512 B2
(45) Date of Patent: Jan. 27, 2015

(54) PROCESSES FOR SYNTHESIZING ALKALINE PHOSPHATASE CONJUGATES

(75) Inventors: Chungen Qian, Shenzhen (CN); Ke Li, Shenzhen (CN); Yuping Zhang, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 47 days.

(21) Appl. No.: 13/151,876

(22) Filed: Jun. 2, 2011

(65) Prior Publication Data

US 2011/0300601 A1  Dec. 8, 2011

(30) Foreign Application Priority Data

Jun. 4, 2010  (CN) .......................... 2010 1 0192646

(51) Int. Cl.
| | | |
|---|---|---|
| C12N 9/00 | (2006.01) | |
| C12N 9/96 | (2006.01) | |
| C07K 1/00 | (2006.01) | |
| G01N 33/535 | (2006.01) | |
| C12Q 1/42 | (2006.01) | |

(52) U.S. Cl.
CPC ................ G01N 33/535 (2013.01); C12Q 1/42 (2013.01)
USPC ............................ 435/188; 435/183; 530/350

(58) Field of Classification Search
None
See application file for complete search history.

(56) References Cited

U.S. PATENT DOCUMENTS

| | | | |
|---|---|---|---|
| 4,808,521 | A | 2/1989 | Allen |
| 5,093,231 | A | 3/1992 | Hoke |
| 5,998,156 | A | 12/1999 | Sugiyama et al. |
| 6,218,160 | B1 | 4/2001 | Duan |
| 6,669,963 | B1 | 12/2003 | Kampinga |
| 6,767,716 | B2 | 7/2004 | Giri |
| 7,078,172 | B1 | 7/2006 | Okamura et al. |
| 2003/0190760 | A1 | 10/2003 | Watkins et al. |
| 2004/0197885 | A1 | 10/2004 | Ueda et al. |
| 2006/0051809 | A1 | 3/2006 | Nazarenko et al. |
| 2007/0141645 | A1 | 6/2007 | Okamura et al. |
| 2008/0254492 | A1 | 10/2008 | Tsuchiya et al. |
| 2009/0269825 | A1 | 10/2009 | Kishimoto et al. |
| 2011/0159565 | A1 | 6/2011 | Qian et al. |
| 2011/0300602 | A1 | 12/2011 | Qian et al. |

FOREIGN PATENT DOCUMENTS

| | | |
|---|---|---|
| CN | 1120457 | 4/1996 |
| CN | 1381725 | 11/2002 |
| CN | 1683407 | 10/2005 |
| CN | 1986785 | 6/2007 |
| CN | 100353166 | 12/2007 |
| EP | 0709458 | 5/1996 |
| EP | 0794249 | 9/1997 |
| EP | 0702712 | 12/1998 |
| EP | 1978363 | 2/2008 |
| JP | 2003009857 | 1/2003 |
| WO | WO2007055284 | 5/2007 |

OTHER PUBLICATIONS

Lombardi et al. Anal Biochem. Aug. 1, 2004;331(1):40-5.*
Tan et al. Biosens Bioelectron. Aug. 15, 2010;25(12):2644-50. Epub May 4, 2010.*
Steidler et al. Appl Environ Microbiol. Jan. 1998;64(1):342-5.*
U.S. Appl. No. 13/152,083, filed Jun. 2, 2011, Qian et al.
Journal of Nanton Medical College 1996:16(2); pp. 162-164.
Restriction Requirement dated Jul. 11, 2012 for U.S. Appl. No. 12/980,870.
Office Action dated Oct. 26, 2012 for U.S. Appl. No. 12/980,870.
Govardhan, 'Crosslinking to Enzymes for Improved Stability and Performance', Current Opinion Biotechnol, vol. 10, pp. 331-335, 1999.
Beiniarz et al., 'Alkaline Phosphatase Activatable Polymeric Cross-Linkers and Their Use in the Stabilization of Proteins', Bioconjugate Chemistry, vol. 9, pp. 390-398, 1998.
Beiniarz et al., 'Technical Notes: Thermally Stabilized Immunoconjugates: Conjugation of Antibodies to Alkaline Phsphatase Stabilized with Polymeric Cross-Linkers', Bioconjugate Chemistry, vol. 9, pp. 399-402, 1998.
Office Action dated Nov. 29, 2012 for U.S. Appl. No. 13/152,083.
Haines, 'Non-Equivalence of D- and L-Trehalose in Stabilizing Alkaline Phosphatase Against Freeze-Drying and Thermal Stress. Is Chiral Recognition Involved?', Organic and Biomolecular Chemistry, vol. 4, pp. 702-706, 2006.
Office Action dated Jun. 7, 2013 for U.S. Appl. No. 12/980,870.

* cited by examiner

*Primary Examiner* — Christian Fronda
(74) *Attorney, Agent, or Firm* — Kory D. Christensen; Matthew S. Bethards; Stoel Rives LLP

(57) ABSTRACT

Methods for synthesizing an ALP conjugate are provided. The methods may include activating a carboxyl group of the ALP with a carbodiimide, to generate an active ester; and adding the substance to be conjugated such that a synthetic reaction occurs between the active ester and the substance to be conjugated, to generate an ALP conjugate.

12 Claims, 2 Drawing Sheets

PROCESSES FOR SYNTHESIZING ALKALINE PHOSPHATASE CONJUGATES

RELATED APPLICATIONS

This application claims priority to Chinese Patent Application No. 201010192646.6, filed Jun. 4, 2010, for "PROCESS FOR SYNTHESIZING ALKALINE PHOSPHATASE CONJUGATE," the disclosure of which is fully incorporated herein by reference.

TECHNICAL FIELD

The present disclosure relates to methods for preparing an enzyme conjugate, specifically, to methods for synthesizing alkaline phosphatase (ALP) conjugates.

DETAILED DESCRIPTION

Figure 1:
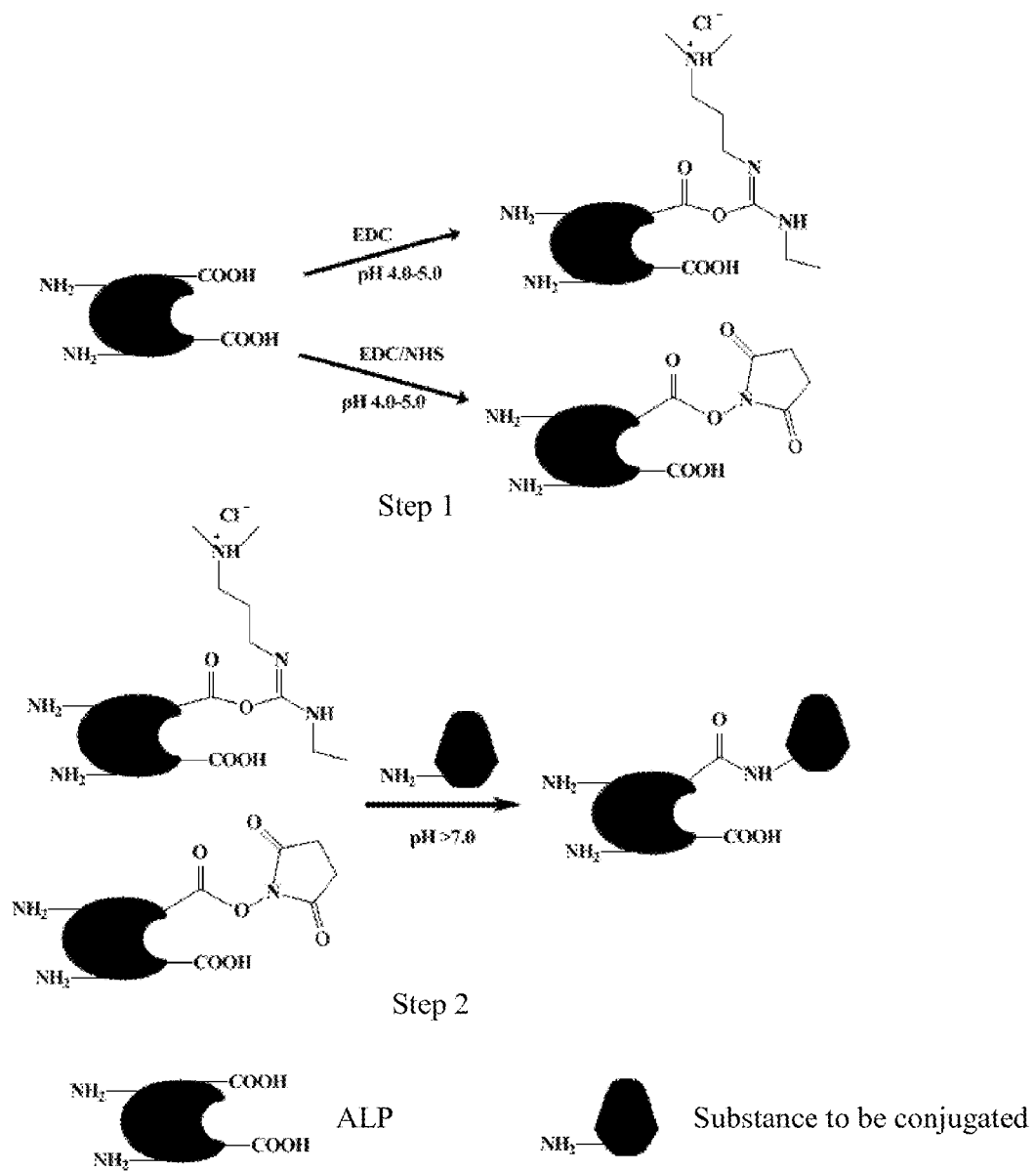
FIG. 1 shows a reaction scheme for an embodiment of the methods according to the present disclosure.

Alkaline phosphatase (ALP) is an enzyme present in, for example, many animals, plants, and microorganisms. ALP may be extracted from calf intestinal mucosa or *E. coli*, and contains multiple isoenzymes. In an appropriate buffer, ALP may catalyze the hydrolysis of chromogenic and chemiluminescent substrates which contain a phosphate group, such as nitrophenyl phosphate (PNP), sodium β-glycerophosphate, naphthyl phosphate, and 3-(2-spiroadamantane)-4-methoxy-4-(3-phosphoryloxy)phenyl-1,2-dioxetane (AMPPD). As such, ALP may be used in clinical immunodiagnosis as a labeling enzyme.

Conjugates of ALP may be formed by coupling ALP to another substance through chemical synthetic methods, referred to as ALP conjugates. ALP conjugates which may be used in immunodiagnosis include ALP-antigen conjugates, ALP-antibody conjugates, and ALP-Staphylococcus protein A (SPA) conjugates. The quality of the ALP conjugate is directly related to the success of the immunoenzymatic technique. ALP conjugates may be used in immunoassay and quantitative analyses, including Western blotting, enzyme linked immunosorbent assay (ELISA), chemiluminescence enzyme immunoassay (CLEIA), and immunohistochemistry.

Methods of synthesizing enzyme conjugates include the following three types: glutaraldehyde (GA) cross-linking methods, oxidation with periodate, and succinimide-maleimide cross-linking methods.

Glutaraldehyde (GA) Cross-Linking Methods.

Glutaraldehyde (GA) is a bifunctional reagent which can link an enzyme via an amino group of the substance to be conjugated. ALP conjugates may be synthesized using GA. The synthetic methods used include one-step methods and two-step methods. In a one-step method, GA may be added directly to a mixture of the ALP and the substance to be conjugated, to obtain an ALP conjugate. In a two-step method, the ALP may be first reacted with GA, and then reacted with the substance to be conjugated after removing excess GA through dialysis, to form the ALP conjugate. Alternatively, the substance to be conjugated may be first reacted with GA, and then linked to the ALP. The activity and the binding rate of the ALP conjugates synthesized using these methods may be unacceptable, however, which can reduce the sensitivity of immunoassays performed using an ALP conjugate made via this method.

Oxidation with Periodate.

This method can be used with enzymes having a high saccharide content. Horseradish peroxidase, for example, may be labeled by this method. In the reaction, hydroxyl groups on the surface polysaccharides of the horseradish peroxidase are oxidized by sodium periodate, to provide highly active aldehyde groups. The aldehyde groups can react with the amino groups on the substance to be conjugated, to form a Schiff base. The substance is thus conjugated with the horseradish peroxidase. As the process of this method may be complex depending upon the enzyme used, the activity of the enzyme conjugate may be significantly lost after synthesis.

Succinimide-Maleimide Cross-Linking Methods.

A heterologous bifunctional crosslinking reagent having a succinimide ester capable of reacting with an amino group, as well as a maleimide group capable of reacting with a mercapto group, may be used in the preparation of an ALP conjugate. Crosslinking reagents of this type include 4-(N-maleimidomethyl)cyclohexane-1-carboxylate N-hydroxysuccinimide ester (SMCC) and a water soluble analog thereof, 4-(N-Maleimidomethyl)cyclohexane-1-carboxylate sulfo-N-hydroxysuccinimide ester (sulfo-SMCC). These crosslinking reagents can activate an amino group on the ALP, to obtain an ALP having a maleimide group, and the maleimide group can then react with a mercapto group on the substance to be conjugated, to obtain an ALP conjugate. However, the reagents used for these methods can be expensive, and the substance to be conjugated generally needs to be thiolated.

Therefore, new methods of synthesizing ALP conjugates having high binding rates and a high activity may be useful.

The present disclosure relates to methods for synthesizing ALP conjugates. Merely for illustration, the methods of the present disclosure may be referred to as carbodiimide methods. The methods of the present disclosure include: step a), activating a carboxyl group of ALP with a carbodiimide and an optional hydroxysuccinimide, to generate an active ALP ester; and step b), optionally adjusting the pH value of the system to be basic, and adding the substance to be conjugated such that a synthetic reaction occurs between the ALP ester and the substance to be conjugated, to generate an ALP conjugate.

In a second aspect, the present disclosure relates to an ALP conjugate obtained using the methods of the present disclosure.

In a third aspect, the present disclosure relates to a kit for labeling a substance with ALP, which includes a carbodiimide and an optional pH adjusting agent. The kit may further include instructions for an operator, a centrifugal ultrafiltration tube, or both.

The term "ALP" as used herein refers to an enzyme capable of dephosphorylating a corresponding substrate, that is, capable of removing a phosphate group from the substrate molecule by hydrolyzing a phosphomonoester, and thereby generating a phosphate ion and a free hydroxyl group. The substrate may be, for example, a nucleic acid, a protein, or an alkaloid. The process of removing the phosphate group is called dephosphorylation. The ALP may have a maximum activity in a basic environment. For example, ALP derived from bacteria may have an optimal pH value of 8.0, and ALP derived from bovines may have an optimal pH value of 8.5. ALP suitable for the methods of the present disclosure may be from various sources, including but not limited to, ALP which is extracted from natural tissue or prepared through the expression of engineered bacterium, ALP which is glycosylated or deglycosylated on its surface, or ALP which is modified in some other manner. All suitable ALPs are included in the present disclosure.

The term "carbodiimide" as used herein refers to a compound having the functional group N═C═N. A carbodiimide may be used as a dehydrating agent, and may also be used in organic synthesis for activating a carbonyl group and promoting the generation of an amide and an ester. Various carbodiimides can be used for the methods disclosed herein, which include but are not limited to, dicyclohexylcarbodiimide (DCC), 1-(3-dimethylaminopropyl)-3-ethyl carbodiimide (EDC), and N,N'-diisopropylcarbodiimide (DIC). All suitable carbodiimides are included in the present disclosure.

The term "hydroxysuccinimide" as used herein refers to a compound having the following structure:

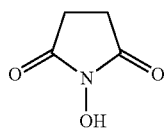

in which the hydroxyl group may be further substituted with other groups. All suitable hydroxysuccinimides can be used for the methods disclosed herein, including but not limited to, N-hydroxysuccinimide (NHS) and sulfo-N-hydroxysuccinimide (sulfo-NHS). Without being bound by theory, it is believed that the hydroxysuccinimide used in the present disclosure improves the yield of the crosslinking reaction with the carbodiimide and reduces the occurrence of side reactions.

The term "acidic" as used herein refers to an environment having a pH lower than about 7. The step of reacting the carbodiimide and the ALP in the methods of the present disclosure may be carried out at an acidic pH. For example, the acidic condition may be an acidic environment having a pH of about 4.0 to about 5.0. Without being bound by theory, it is believed that, when the reaction occurs under acidic conditions, the reactivity of the carbodiimide with the carboxyl group is higher, and the self-crosslinking reactions of the ALP or the antibody are reduced, thus improving the synthetic yield and maintaining the activity of the ALP conjugate.

The term "substance to be conjugated" as used herein refers to various substances which may be labeled by ALP. These substances include, but are not limited to, various peptides and proteins, including amino-containing peptides and proteins. The peptides and proteins which can be the substance to be conjugated in the present disclosure include antigens such as triiodothyronine and thyroxine, or antibodies including various monoclonal antibodies, polyclonal antibodies, and antibody segments derived from animals. All suitable peptides, proteins, and other substances to be conjugated are included in the methods of the present disclosure.

The term "pH adjusting agent" as used herein refers to a substance which may be used to adjust the pH value. Such pH adjusting agents include, but are not limited to, an acid, including an organic acid or an inorganic acid; a base; a neutralizing agent; and a buffer system. Suitable acids which may be useful in the methods of the present disclosure include: an aliphatic organic acid, for example, a monocarboxylic acid, a dicarboxylic acid, or a polycarboxylic acid, such as tartaric acid, oxalic acid, malic acid, citric acid, and ascorbic acid; an aromatic organic acid, for example, benzoic acid, salicylic acid, and caffeic acid; and an inorganic acid, for example, hydrochloric acid, sulfuric acid, and nitric acid. Suitable bases which may be useful in the methods of the present disclosure include, for example, sodium hydroxide, potassium hydroxide, ammonia, sodium carbonate, sodium bicarbonate, potassium carbonate, and potassium bicarbonate. Suitable buffer systems which may be useful in the methods of the present disclosure include, but are not limited to, a TAE buffer system, a TBE buffer system, an EDTA buffer system, an EGTA buffer system, a Tris-HCl buffer system, a citrate buffer system, a phosphate buffer system, an acetate buffer system, an SSC buffer system, an SSPE buffer system, a 2-(N-morpholino)ethanesulfonic acid (MES) buffer system, and a piperazine-N,N'-bis(2-ethanesulfonic acid) (PIPES) buffer system.

As noted previously, the methods of the present disclosure include: step a), activating a carboxyl group of ALP with a carbodiimide and an optional hydroxysuccinimide to generate an active ALP ester; and step b), optionally adjusting the pH value of the system to be basic, and adding the substance to be conjugated such that a synthetic reaction occurs between the ALP ester and the substance to be conjugated, to generate an ALP conjugate. Step a) may be carried out under acidic conditions, for example, at a pH of about 4.0 to about 5.0.

For example, in step a), the carboxyl group of the ALP may be reacted first with a carbodiimide to generate an intermediate O-acyl isothiourea, which is similar to introducing an ester group to activate the carboxylic acid. Then, the O-acyl isothiourea may react with an amine to generate the desired products, such as an amide and a urea. In an embodiment, the carbodiimide and the hydroxysuccinimide are used simultaneously. The hydroxysuccinimide may be, for example, N-hydroxysuccinimide (NHS) or sulfo-N-hydroxysuccinimide (sulfo-NHS). N-hydroxysuccinimide is an active amine, and is capable of converting the carboxyl group into a succinyl ester in presence of a dehydrating agent, such as a carbodiimide. The succinyl ester may then react with an amino group to form a stable amide compound. As O-acyl isothiourea compounds are unstable, when NHS is introduced into the reaction system, NHS may capture the unstable reaction intermediate, thus improving the efficiency of generating the ALP active ester. This reaction process is shown in FIG. 1.

The carbodiimide may be EDC, and may be used in a wide concentration range, such as 10-5000 times the moles of the enzyme. The molar ratio of the carbodiimide to the hydroxysuccinimide may be between about 5:1 and about 1:10, for example, between about 2:1 and about 1:5. The carbodiimide may be added as a solid powder or may be formulated into the mother liquor before use.

As the ALP may be unstable at an excessively high or low temperature, the reaction temperature is generally in the range of between about 4° C. to about 37° C., and the reaction time is generally in the range of between about 10 min to about 48 h. Persons of ordinary skill in the art will understand that the reaction temperature correlates with the reaction time, that is, the higher the temperature is, the shorter the reaction time may be.

In the reaction, the pH may influence the reaction rate and efficiency. When the pH is in an acidic range, the carbodiimide has a higher reactivity with the carboxyl group, and less side reactions may occur. In one embodiment of the methods of the present disclosure, the synthesis of the ALP active ester is carried out at a pH between about 4.0 and about 5.0. In order to maintain a pH value, a buffer system such as a 2-(N-morpholino)ethanesulfonic acid (MES) buffer system or a piperazine-N,N'-bis(2-ethanesulfonic acid) (PIPES) buffer system may be used.

In step b), the system is optionally adjusted to become basic before adding the substance to be conjugated. This may help initiate the reaction of the ALP ester and the amino group of the substance to be conjugated, so as to generate the ALP conjugate. With the increased pH value, the stability of the ALP active ester prepared in step a) is decreased, and thus the ALP active ester may more easily react with an amino group on the substance to be conjugated. Therefore, in a basic environment, the ALP active ester more efficiently generates an ALP conjugate, as is shown in FIG. 1.

In one embodiment, step b) is carried out in a basic environment having a pH of higher than about 7.0. In another embodiment, this step is performed at a pH range of between about 7.5 and about 9.0. In order to maintain the desired pH value, a buffer system may be used. The buffer system may be, for example, a phosphate buffer system, a 2-(N-morpholino)ethanesulfonic acid (MES) buffer system, or a piperazine-N,N'-bis(2-ethanesulfonic acid) (PIPES) buffer system. In another embodiment, the pH adjusting agent of step b) may be a base, for example, sodium hydroxide, potassium hydroxide, ammonia, sodium carbonate, sodium bicarbonate, potassium carbonate, and potassium bicarbonate.

As the ALP or substance to be conjugated may be unstable at an excessively high or low temperature, the reaction temperature is generally in the range of between about 4° C. to about 37° C., and the reaction time is in the range of between about 10 min to about 48 h. Persons of ordinary skill in the art will understand that the reaction temperature correlates with the reaction time, that is, the higher the temperature is, the shorter the reaction time may be.

Optionally, after the synthesis of the ALP conjugate, the conjugate may be purified via ultrafiltration, a desalting column, dialysis, gel filtration, Protein A or G affinity column chromatography, or ammonium sulfate precipitation. In an embodiment, the ALP conjugate is purified by Protein A or G affinity column chromatography.

As the substance to be conjugated may avoid mercaptoacetic processes, such as that used in the succinimide-maleimide cross-linking process, the methods of the present disclosure are comparatively simpler and may be performed at a lower cost.

According to the description herein, persons of skill in the art will understand that an ALP conjugate obtained by the methods of the present disclosure may retain a high activity of the ALP and the substance to be conjugated, thus providing a highly sensitive ALP conjugate reagent. For example, an ALP conjugate obtained by the methods of the present disclosure may be applicable in various immunoassays which utilize ALP.

In a further aspect, the present disclosure provides a kit for labeling with ALP. The kit of the present disclosure includes a carbodiimide and an optional hydroxysuccinimide, which are selected according to the description herein. In one embodiment, the kit further includes a pH adjusting agent. In another embodiment, the pH adjusting agent includes the pH adjusting agent of step a), the pH adjusting agent of step b), or both, in which the pH adjusting agent of step a) and the pH adjusting agent of step b) may be the same or different. Any suitable pH adjusting agent may be used in the present disclosure. For example, the pH adjusting agent of step a) or b) may be a buffer system, an acid, or a base. In one embodiment, the pH adjusting agent of step a) may be an acid or a buffer system, for example, a 2-(N-morpholino)ethanesulfonic acid (MES) buffer system or a piperazine-N,N'-bis(2-ethanesulfonic acid) (PIPES) buffer system. In another embodiment, the pH adjusting agent of step b) may be a base, for example, sodium hydroxide, potassium hydroxide, ammonia, sodium carbonate, sodium bicarbonate, potassium carbonate, and potassium bicarbonate.

In one embodiment, the kit further includes a manual which instructs an operator how to use the methods of the present disclosure, a centrifugal ultrafiltration tube, or both.

Persons of skill in the art will understand that the aspects and features described herein may be combined, and various embodiments formed thereby are included in the present disclosure.

The present disclosure is illustrated with reference to the following Examples, which are not intended to be limiting. The reagents used in the Examples are analytical grade and obtained from Sigma-Aldrich Corporation, unless otherwise stated.

Example 1

An amount of ALP was dissolved in 80 μL of 30 mM MES buffer (pH 4.0), EDC and NHS were added, and the solution was diluted to 100 μl by MES buffer, wherein the final concentrations of ALP, EDC, and NHS were 0.01 mmol/L, 10 mmol/L, and 50 mmol/L, respectively. After reaction for 1 hour at 25° C., 100 μg of mouse anti-human prolactin monoclonal antibody and 100 μL of phosphate buffer (pH 8.0) were added to the solution, and the pH of the solution was adjusted to 8.0 with 3 mol/L NaOH solution. After reaction for 2 hours at 37° C., the solution was purified by a Protein G affinity column (obtained from GE Company) to obtain an ALP-prolactin antibody conjugate.

Example 2

An amount of ALP was dissolved in 80 μL of 30 mM MES buffer (pH 5.0), EDC and NHS were added, and the solution was diluted to 100 μl by MES buffer, wherein the final concentrations of ALP, EDC, and NHS were 0.01 mmol/L, 100 mmol/L, and 50 mmol/L, respectively. After reaction for 1 hour at 25° C., 100 μg of mouse anti-human prolactin monoclonal antibody and 100 μL of phosphate buffer (pH 8.0) were added to the solution, and the pH of the solution was adjusted to 8.0 with 3 mol/L NaOH solution. After reaction for 3 hours at 25° C., the solution was purified by a Protein G affinity column (obtained from GE Company) to obtain an ALP-prolactin antibody conjugate.

Example 3

An amount of ALP was dissolved in 80 μL of 30 mM MES buffer (pH 5.0), EDC and NHS were added, and the solution was diluted to 100 μl by MES buffer, wherein the final concentrations of ALP, EDC, and NHS were 0.01 mmol/L, 10 mmol/L, and 50 mmol/L, respectively. After reaction for 10 minutes at 37° C., 100 μg of mouse anti-human prolactin monoclonal antibody and 100 μL of phosphate buffer (pH 9.0) were added to the solution, and the pH of the solution was adjusted to 9.0 with 3 mol/L NaOH solution. After reaction for 2 hours at 37° C., the solution was purified by a Protein G affinity column (obtained from GE Company) to obtain an ALP-prolactin antibody conjugate.

Example 4

An amount of ALP was dissolved in 80 μL of 30 mM MES buffer (pH 5.0), EDC was added, and the solution was diluted to 100 μl by MES buffer, wherein the final concentrations of ALP and EDC were 0.01 mmol/L and 100 mmol/L, respectively. After reaction for 10 minutes at 37° C., 100 μg of mouse anti-human prolactin monoclonal antibody and 100 µL of phosphate buffer pH (8.0) were added to the solution, and the pH of the solution was adjusted to 8.0 with 3 mol/L NaOH solution. After reaction for 20 hours at 4° C., the solution was purified by a Protein G affinity column (obtained from GE Company) to obtain an ALP-prolactin antibody conjugate.

Example 5

An amount of ALP was dissolved in 80 µL of 30 mM MES buffer (pH 5.0), EDC and NHS were added, and the solution was diluted to 100 µl by MES buffer, wherein the final concentrations of ALP, EDC, and NHS were 0.01 mmol/L, 0.1 mmol/L, and 0.1 mmol/L, respectively. After reaction for 10 minutes at 37° C., 100 µg of mouse anti-human prolactin monoclonal antibody and 100 µL of phosphate buffer (pH 8.0) were added to the solution, and the pH of the solution was adjusted to 8.0 with 3 mol/L NaOH solution. After reaction for 20 hours at 4° C., the solution was purified by a Protein G affinity column (obtained from GE Company) to obtain an ALP-prolactin antibody conjugate.

Example 6

An amount of ALP was dissolved in 80 µL of 30 mM MES buffer (pH 5.0), EDC and NHS were added, and the solution was diluted to 100 µl by MES buffer, wherein the final concentrations of ALP, EDC, and NHS were 0.01 mmol/L, 10 mmol/L, and 2 mmol/L, respectively. After reaction for 10 minutes at 37° C., 100 µg of mouse anti-human prolactin monoclonal antibody and 100 µL of phosphate buffer (pH 8.0) were added to the solution, and the pH of the solution was adjusted to 8.0 with 3 mol/L NaOH solution. After reaction for 20 hours at 4° C., the solution was purified by a Protein G affinity column (obtained from GE Company) to obtain an ALP-prolactin antibody conjugate.

Comparative Example 7

In this Comparative example, the glutaraldehyde (GA) cross-linking method was adopted. An amount of ALP was incorporated into 0.2 mL of 1.25% GA made by diluting 25% GA with 0.01 mol/L PB (phosphate buffer), pH 6.8, at a final concentration of 0.01 mmol/L. After reaction for 18 hours at room temperature (about 20° C.), the solution was purified on a Sephadex G-50 gel column which had been equilibrated with 0.15 mol/L NaCl, and free GA was removed to obtain a purified hydroformylated enzyme solution. One hundred µg of mouse anti-human prolactin monoclonal antibody was dissolved in 1 mL of 0.15 mol/L NaCl, then mixed with the purified hydroformylated enzyme solution having an ALP concentration of about 10 mg/mL. 0.1 mL of 1 mol/L carbonate buffer (pH 9.6) was added and the solution was stirred under 4° C. for 24 hours. 0.1 mL of 0.2 mol/L lysine (0.29 g lysine dissolved in 10 mL of distilled water) was added, and placed at 4° C. for 2 hours, to block any remaining aldehyde groups so as to quench the reaction. The reaction solution was purified by a Protein G affinity column (obtained from GE Company), to obtain an ALP-prolactin antibody conjugate.

Comparative Example 8

In this Comparative example, the periodate oxidation method was adopted. An amount of ALP was incorporated into 1 mL of 0.3 mol/L carbonate buffer (pH 8.0) at a final concentration of 0.01 mmol/L. 0.1 mL of a 1% (v/v) dinitrofluorobenzene solution in anhydrous ethanol was added, and the solution was stirred in dark at room temperature for 1 hour. Next, 1 mL of 0.06 mol/L $NaIO_4$ solution was added and the solution was stirred for another 30 minutes, then 1 mL of 0.1616 mol/L ethylene glycol was added and the solution was further stirred in dark for an additional 1 hour. The solution was dialyzed against 0.01 mol/L carbonate buffer (pH 9.0-9.5) at 4° C. overnight, and the buffer was exchanged during dialysis. One hundred µg of mouse anti-human prolactin monoclonal antibody, dissolved in $NaHCO_3$ solution (pH 9.0-9.5), was added to the dialyzed solution, and stirred at room temperature in the dark for 2 hours. Five mg of $NaBH_4$ solution was added and reacted at 4° C. overnight. The resulting solution was purified with a Protein G affinity column (obtained from GE Company) to obtain an ALP-prolactin antibody conjugate.

Example 9

The ALP-mouse anti-human prolactin monoclonal antibody conjugates obtained in Examples 1-8 were used in a human prolactin chemiluminescence enzyme immunoassay, in triplicate. For each assay, 50 µg of magnetic beads coated with a prolactin antibody were added to a 200 ng/mL prolactin sample, and 0.4 µmol of an ALP-prolactin antibody conjugate (prepared in Examples 1-8) were added. The solutions were incubated and washed. Two hundred µl of a chemiluminescent liquid, Lumiphos 530 (Beckman Coulter Inc.), were added, and the luminescence intensities of the solutions were measured with a Hamamatsu 9507 semi-automatic chemiluminescence analyzer (Beijing Hamamatsu Photon Techniques Inc.). An average chemiluminescence intensity was calculated for each Example conjugate, as shown in Table 1. It was found that the higher the luminescence intensity obtained in the immunoassay, the higher the immunoactivity and ALP activity of the ALP antibody conjugate.

TABLE 1

Results of the human prolactin assay with the ALP antibody conjugates prepared in Examples 1-8

| Enzyme Conjugate | Averaged Luminescence Intensity (RLU), 200 ng/mL Prolactin |
|---|---|
| Enzyme conjugate of Example 1 | 491316 |
| Enzyme conjugate of Example 2 | 624578 |
| Enzyme conjugate of Example 3 | 548089 |
| Enzyme conjugate of Example 4 | 377980 |
| Enzyme conjugate of Example 5 | 426587 |
| Enzyme conjugate of Example 6 | 489456 |
| Enzyme conjugate prepared with GA method (Comparative example 7) | 156519 |
| Enzyme conjugate prepared with sodium periodate method (Comparative Example 8) | 97606 |

As shown in Table 1, the ALP antibody conjugates prepared using the methods of the present disclosure have a better immunoactivity and ALP activity than those prepared via conventional methods.

Example 10

An amount of ALP was dissolved in 80 µL of 30 mM MES buffer (pH 5.0), EDC and NHS were added, and the solution was diluted to 100 µl by MES buffer, wherein the final concentrations of ALP, EDC, and NHS were 0.01 mmol/L, 10 mmol/L, and 2 mmol/L, respectively. After reaction for 10 minutes at 37° C., 100 μg of triiodothyronine (TSH), which was dissolved in DMF, and 100 μl of phosphate buffer (pH 8.0) were added, and the pH of the solution was adjusted to 8.0 with 3 mol/L NaOH solution. After reaction for 2 hours at 37° C., the solution was purified by ultrafiltration in a 15 mL ultrafiltration tube whose cut-off molecular weight was 30 kDa (obtained from Millipore Company) with 30 mM MES buffer (pH 6.0) as a replacement buffer. An ALP-triiodothyronine conjugate was obtained.

Comparative Conjugate

ALP with a final concentration of 0.01 mmol/L was dissolved in 0.2 mL of 1.25% GA made by diluting 25% GA with 0.01 mol/L PB (phosphate buffer) (pH 6.8). After reaction for 18 hours at room temperature (about 20° C.), the solution was purified on a Sephadex G-50 gel column equilibrated with 0.15 mol/L NaCl, and free GA was removed to obtain a purified hydroformylated enzyme solution. One hundred μg of triiodothyronine, which was dissolved in 1 mL of DMF, was mixed with the purified hydroformylated enzyme solution. 0.1 mL of 1 mol/L carbonate buffer (pH 9.6) was added, the pH was adjusted to 9.6, and the solution was stirred under 4° C. for 24 hours. 0.1 mL of 0.2 mol/L lysine (0.29 g lysine dissolved in 10 mL of distilled water) was added, and placed at 4° C. for 2 hours, to block any remaining aldehyde groups so as to quench the reaction. The reaction solution was purified by ultrafiltration in a 15 mL ultrafiltration tube whose cut-off molecular weight was 30 kDa (obtained from Millipore Company), with 30 mM MES buffer (pH 6.0) as a replacement buffer. An ALP-triiodothyronine conjugate synthesized via the GA method was obtained.

The magnetic beads coated with triiodothyronine monoclonal antibody were added to the ALP-triiodothyronine conjugate solutions prepared via the two methods described. The solutions were incubated and washed. A chemiluminescent liquid was added to each, and the luminescence intensities of the solutions were measured with a Hamamatsu 9507 semi-automatic chemiluminescence analyzer, as shown in Table 2.

TABLE 2

Results of the assay with ALP antigen conjugates.

| Enzyme conjugate | Luminescence Intensity (RLU) |
|---|---|
| Enzyme conjugate of Example 10 | 2136560 |
| Enzyme conjugate prepared with GA method | 104813 |

It is seen in Table 2 that the ALP antigen conjugate prepared via the methods of the present disclosure has a better immunoactivity than that prepared via the GA cross-linking method.

Example 11

The ALP-prolactin antibody conjugate obtained in Example 2 was used in a chemiluminescence enzyme immunoassay of human prolactin. To a series of prolactin samples at various concentrations, an equivalent amount of magnetic beads coated with a prolactin antibody and the ALP-prolactin antibody conjugate were added. The resulting solution was incubated and washed. A chemiluminescent liquid was added, and the luminescence intensities of the solutions were measured with a Hamamatsu 9507 semi-automatic chemiluminescence analyzer, as shown in Table 3.

TABLE 3

Results of the chemiluminescence enzyme immunoassay of various concentrations of prolactin.

| Prolactin Concentration (ng/mL) | Luminescence Intensity (RLU) |
|---|---|
| 0 | 4189 |
| 2 | 15831 |
| 10 | 68944 |
| 20 | 126217 |
| 100 | 621691 |
| 200 | 1311346 |

With the prolactin concentration as the X axis and the luminescence intensity as the Y axis, a linear fit of concentration versus luminescence intensity was performed using the least squares method. The linear correlation coefficient was 0.9993, as shown in FIG. 2.

Figure 2:
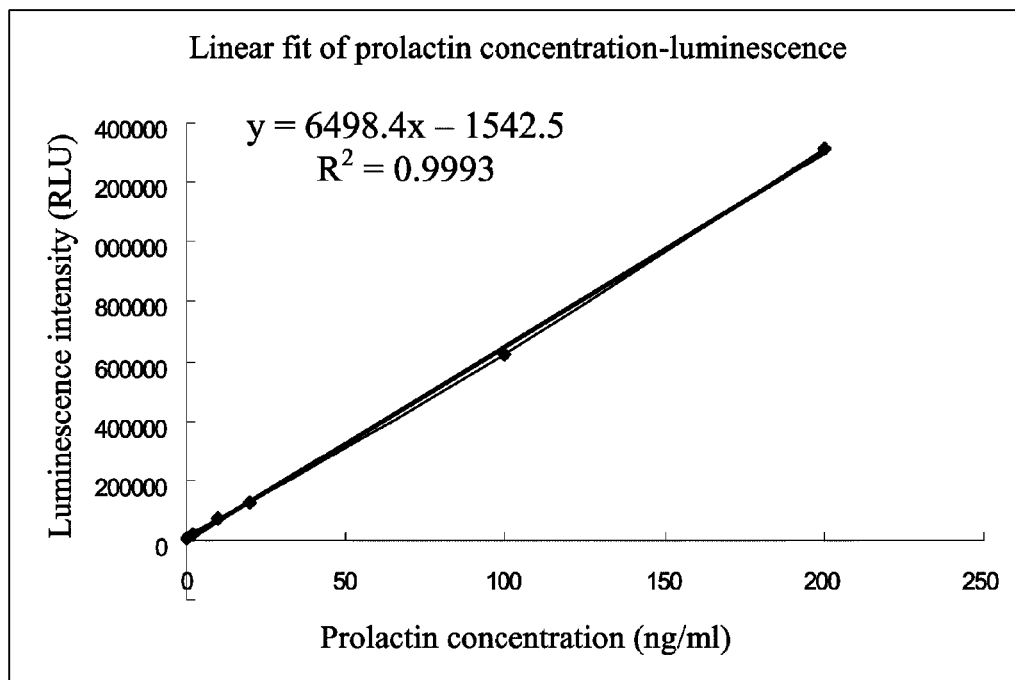
FIG. 2 shows a linear fit of an antibody concentration v. luminescence intensity correlation obtained by an exemplary ALP-antibody conjugate according to the present disclosure.

As shown in Table 3 and FIG. 2, an ALP-prolactin antibody conjugate synthesized by the methods of the present disclosure has suitable effects when being applied in a quantitative immunoassay.

Those skilled in the art will recognize, or be able to ascertain using no more than routine experimentation, equivalents to the specific embodiments of the invention described herein. Such equivalents are intended to be encompassed by the following claims.

The invention claimed is:

1. A method of synthesizing an alkaline phosphatase ("ALP") conjugate, comprising:
   activating a carbonyl group of ALP with a carbodiimide under acidic conditions to form an active ALP ester; and
   adding a substance to be conjugated under basic conditions; wherein the active ALP ester reacts with the substance to be conjugated to generate an ALP conjugate.

2. The method of claim 1, wherein activating of a carbonyl group further comprises adding a hydroxysuccinimide.

3. The method of claim 1, wherein the substance to be conjugated is selected from at least one of the following: a peptide, a protein, an antigen, an antibody, and *Staphylococcus* protein A.

4. The method of claim 1, wherein the acidic conditions range between about pH 4.0 and about pH 5.0.

5. The method of claim 1, wherein the carbodiimide is selected from at least one of the following: dicyclohexylcarbodiimide (DCC), 1-(3-dimethylaminopropyl)-3-ethylcarbodiimide (EDC), and N,N'-diisopropylcarbodiimide (DIC).

6. The method of claim 2, wherein the hydroxysuccinimide is selected from at least one of the following: N-hydroxysuccinimide (NHS) and sulfo-N hydroxysuccinimide (sulfo-NHS).

7. The method of claim 1, wherein the basic conditions range between about pH 7.5 and about pH 9.0.

8. The method of claim 1, further comprising purifying the ALP conjugate.

9. The method of claim 8, wherein purifying the ALP conjugate comprises using at least one of the following for purification: ultrafiltration, a desalting column, dialysis, gel filtration, Protein A or G affinity column chromatography, and ammonium sulfate precipitation.

10. A method of synthesizing an enzyme conjugate, comprising:
    activating a carbonyl group of an enzyme with a carbodiimide, under acidic conditions between about pH 4.0 and about pH 5.0, to form an active ester; and
    adding a substance to be conjugated selected from at least one of the following: a peptide, a protein, an antigen, an antibody, and *Staphylococcus* protein A, under basic conditions between about pH 7.5 and about pH 9.0;

wherein the active ester reacts with the substance to be conjugated to generate an enzyme conjugate.

11. The method of claim 10, wherein activating of a carbonyl group further comprises adding a hydroxysuccinimide.

12. The method of claim 11, wherein the carbodiimide is selected from at least one of the following: dicyclohexylcarbodiimide (DCC), 1-(3-dimethylaminopropyl)-3-ethylcarbodiimide (EDC), and N,N'-diisopropylcarbodiimide (DIC); and wherein the hydroxysuccinimide is selected from at least one of the following: N-hydroxysuccinimide (NHS) and sulfo-N-hydroxysuccinimide (sulfo-NHS).

* * * * *